United States Patent [19]
Mitchell

[11] Patent Number: 5,751,422
[45] Date of Patent: May 12, 1998

[54] IN-SITU PARTICLE DETECTION UTILIZING OPTICAL COUPLING

[75] Inventor: John R. Mitchell, Boulder, Colo.

[73] Assignee: Particle Measuring Systems, Inc., Boulder, Colo.

[21] Appl. No.: 606,891

[22] Filed: Feb. 26, 1996

[51] Int. Cl.⁶ .................................. G01N 21/00
[52] U.S. Cl. ........................................... 356/337
[58] Field of Search ........................ 356/335–339, 356/73; 372/107, 108, 109, 75, 69

[56] References Cited

U.S. PATENT DOCUMENTS

| | | |
|---|---|---|
| Re. 34,729 | 9/1994 | Sipes, Jr. . |
| 4,571,079 | 2/1986 | Knollenberg . |
| 4,594,715 | 6/1986 | Knollenberg . |
| 4,665,529 | 5/1987 | Baer et al. . |
| 4,685,802 | 8/1987 | Saito et al. . |
| 4,723,257 | 2/1988 | Baer et al. . |
| 4,753,530 | 6/1988 | Knight et al. ............... 356/73 |
| 4,798,465 | 1/1989 | Knollenberg . |
| 4,896,048 | 1/1990 | Borden . |
| 5,092,675 | 3/1992 | Sommer . |
| 5,467,188 | 11/1995 | Miyashita .................. 356/336 |

FOREIGN PATENT DOCUMENTS

| | | |
|---|---|---|
| 0015170 A1 | 1/1980 | European Pat. Off. . |

OTHER PUBLICATIONS

R.G. Knollenberg, "Measurement of Particle Sizes Below 0.1 Micrometers", Journal of Environmental Science, Jan.–Feb. 1985.

Primary Examiner—K. Hantis
Attorney, Agent, or Firm—Duft, Graziano & Forest, P.C.

[57] ABSTRACT

A resonant optical cavity having a laser medium therein is positioned within a specific environment, such as a process and/or harsh environment, and a sensing region, also within the resonant optical cavity, receives light whereby particles at the sensing region affect, as by scattering, light at the sensing region. The affected light is optically collected within the specific environment and optically coupled to a processor outside the specific environment where an output is provided that is indicative of particles detected at the sensing region, including small particles having a size at least as small as about 0.05 to 10 microns. With a solid state laser medium utilized within the resonant optical cavity, the solid state laser medium is pumped by an actuator, such as a semiconductor diode laser, providing a light output that is optically coupled to the solid state laser medium. Optical coupling includes fiber optics and lenses for focusing light into and out of the fiber optics, as well as a notch filter through which scattered light is coupled to the processor, and, with the specific environment contained within a housing, an optical feedthrough is utilized to couple light through the housing.

18 Claims, 1 Drawing Sheet

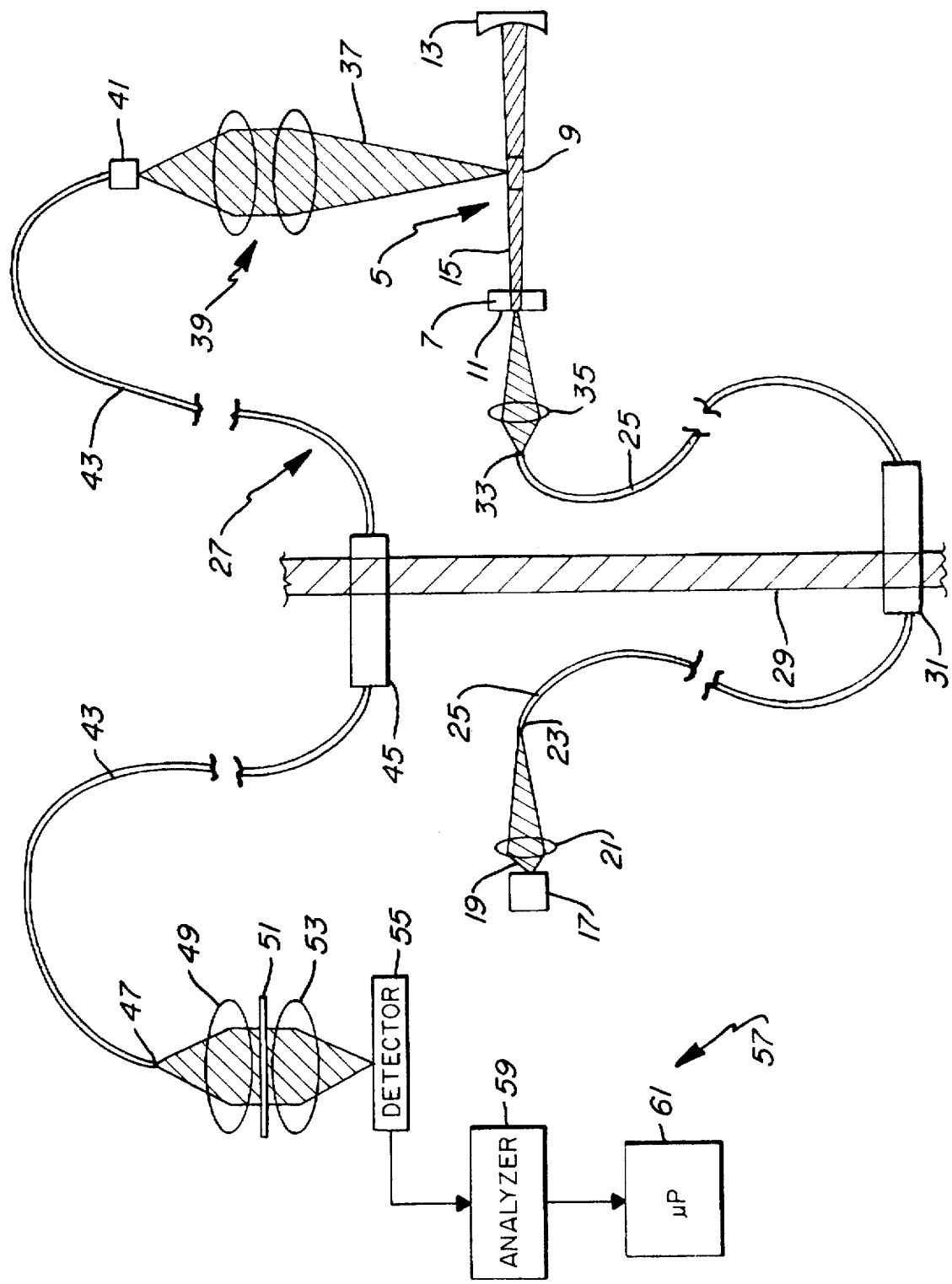

IN-SITU PARTICLE DETECTION UTILIZING OPTICAL COUPLING

FIELD OF THE INVENTION

This invention relates to particle detection, and, more particularly, relates to in-situ particle detection utilizing optical coupling.

BACKGROUND OF THE INVENTION

Particle detection using light scattering is now well known, and such devices are known to detect particles in air as small as, or smaller than, 0.1 microns (see, for example, U.S. Pat. No. 4,798,465, and an article by R. G. Knollenberg entitled "The Measurement of Particle Sizes Below 0.1 Micrometers", Journal of Environmental Science, January–February 1985).

Useful in-situ detection of particles in process tools using light scattering is also now known, and has resulted in reduced costs and improvement in general tool cleanliness. Widespread application of such in-situ monitors has been limited, however, by the technology now used in such monitors.

The ability of a particle detector to monitor contamination in a process tool is normally determined by the minimum detectable particle, the sample, or sensing, region, and the location of the sample region, with best results being produced by monitoring of particles in close proximity to the item, such as a wafer, being processed.

Several different light sources have been heretofore suggested for use, and/or have been used, in monitors, with the most successful being a semiconductor diode laser (SDL) having low cost, small size, and relatively high brightness. The SDL, however, cannot withstand a harsh, or hostile, environment such as is found, for example, in many process tools, and is also limited in power which restricts the minimum particle size that can be detected by a device using light scattering and an SDL as the light source.

Since SDLs cannot withstand a harsh environment such as is found in many process tools, this limits the location of monitors that use the SDL laser and therefore limits their usefulness, as, for example, requiring the sample region to be remotely located, such as by being moved outside the process tool, typically to the exhaust line, and thus being positioned relatively far from the item being processed, and which can result in an additional detection problem since, under low pressure, particles are not transported by the few remaining gas molecules.

While other types of light sources might be used that are vacuum compatible and also able to withstand harsh environments, such as the Helium Neon (HeNe) laser, the output power of such lasers is limited, with the HeNe laser, for example, providing output power that is limited to tens of milliwatts less than that typically produced by a SDL. Moreover, light sources, such as HeNe lasers are relatively large, making them difficult, if not impossible to fit into many process tools. Hence, use of relatively large devices with a lower power light source, such as the HeNe laser, is restricted to use where lower power and larger detection devices can be tolerated.

The SDL is not the only component adversely affected by a process or harsh environment. The performance of electrically active components, such as photodetectors used to transform the light scattered from particles into electrical signals, can also be adversely affected under harsh conditions such as, for example, the presence of high temperatures and/or high magnetic fields within the harsh environment. High temperatures can cause photodetectors to be degraded, or sometimes permanently damaged, and can also cause excessive noise in the detector which can cause false particle counts and/or limit the sensitivity of the detector, while high magnetic fields can also cause false pulse counts and/or limit sensitivity. Thus, it is important that the detectors be isolated from the process and/or harsh environment, which further limits the use of known in-situ detection devices in such environments.

As can be appreciated from the foregoing, now known light sources for use in particle detection devices have limited in-situ performance and reliability, and, in some process tools, the detection device has been found to be ineffective because the particles to be detected are smaller than the detection device is able to detect.

As can also be appreciated from the foregoing, providing particle sensing in a specific environment, such as a process or harsh environment, using a high power light source relative to now known light sources, within the specific environment, would result in improved particle detection.

It is known that a laser medium, such as a solid state laser medium, can be positioned within a resonant cavity and be end-pumped by an actuator, such as a laser diode, the light output of which is optically coupled to the laser medium to provide high power within the cavity (see, for example, U.S. Pat. No. 4,723,257 to Baer et al.). There is no teaching or suggestion in this patent, however, that such a light source might be used in conjunction with a sensing region, also within the resonant cavity, to provide improved particle detection and/or use of such a light source in an in-situ particle detector positioned within a specific environment, such as a process or harsh environment, to provide improved particle detection.

SUMMARY OF THE INVENTION

In-situ particle detection is achieved utilizing optical elements, or components, within a specific environment, such as a process and/or harsh environment, and positioning other elements outside the specific environment, including elements adversely affected by conditions within the specific environment, such as, for example, elements such as solid state and/or electrically active elements adversely affected by conditions such as, again by way of example, high temperatures and/or high magnetic fields, with optical coupling being utilized between the elements within and outside the specific environment.

A sensing region, within the specific environment and capable of having particles thereat, receives light from an optical light source, also within the specific environment, whereby particles at the sensing region affect, as by scattering, light thereat. The affected light is optically collected within the specific environment and optically coupled from the specific environment to a processor, such as a light detector, preferably including one or more photodetectors, and an analyzer, such as a pulse height analyzer, positioned outside the specific environment to thereby enable enhanced in-situ detection of particles, including enhanced detection of small particles having a size at least as small as about 0.05 to 10 microns.

The light source is preferably a resonant optical cavity having a laser medium therein, such as a solid state laser medium, pumped by an actuator, such as a semiconductor diode laser positioned outside the specific environment, and the sensing region is preferably established within the resonant optical cavity.

Optical coupling between the elements within the specific environment and other elements outside the specific environment is preferably achieved by fiber optics and lenses to focus light into and out of the fiber optics and collimate scattered light coupled from the fiber optics, with a filter, preferably a notch filter, being used to couple light to the processor outside the specific environment.

With the specific environment contained within an enclosure by a housing, an optical feedthrough, such as a vacuum feedthrough where a vacuum is established in the specific environment, is preferably used to couple light through the housing into the enclosure.

It is therefore an object of this invention to provide improved particle detection.

It is another object of this invention to provide improved in-situ particle detection utilizing optical coupling.

It is still another object of this invention to provide improved particle detection wherein optical elements are utilized within a specific environment in conjunction with elements necessarily positioned outside the specific environment for enhanced operation.

It is still another object of this invention to provide improved particle detection using a light source and a sensing region within a specific environment, and optically coupling affected, or scattered light to a processor outside the specific environment.

It is another object of this invention to provide improved particle detection using a resonant optical cavity inside a specific environment and a laser medium and a sensing region within the resonant optical cavity to cause particles at the sensing region to affect, or scatter, light thereat.

It is another object of this invention to provide improved particle detection using a resonant optical cavity inside a specific environment and a solid state laser medium within the resonant optical cavity with the solid state laser medium being optically pumped by an actuator positioned outside the specific environment to provide laser light within the resonant cavity to a sensing region, also within the resonant cavity, whereby particles at the sensing region affect, or scatter, light that is optically collected and optically coupled to a processor outside the specific environment.

It is another object of this invention to provide improved in-situ particle detection through optical coupling using fiber optics and associated optical systems to transmit light between elements.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which the single FIGURE shown is a combined sketch and block diagram illustrating the invention.

DESCRIPTION OF THE INVENTION

As shown in the single FIGURE, a resonant optical cavity 5 has a laser medium 7 and a sample, or sensing, region 9 positioned therein. Laser medium 7 is preferably a solid state laser medium, such as a Neodymium doped (1.1% by weight) Yttrium Aluminum Garnate (Nd:YAG), or like-type, crystal, but in some applications, such as, for example, where size and power are not constraints, could be another type of laser, such as, for example, a Helium Neon (HeNe) laser, such as shown, for example, in U.S. Pat. Nos. 4,571, 079 and 4,798,465 to Knollenberg, and, at least in some applications, the cavity utilized could be a passive cavity, such as shown, for example, in U.S. Pat. No. 4,594,715 to Knollenberg.

Resonant optical cavity 5 is of small size and is defined, or established, between end mirrors 11 and 13. End mirror 11 is preferably a planar mirror adjacent to laser medium 7, and preferably is formed as a coating on the outside, or back, wall of a solid state easer medium 7, as indicated in the FIGURE. End mirror 13 is preferably a concave mirror having a curvature of 100 cm and is spaced from mirror 11 a sufficient distance to allow lasing to occur so that laser light 15 builds within resonant optical cavity 5 between the mirrors.

Mirrors 11 and 13 have a high reflectance at the wavelength of the fundamental mode $TEM_{oo}$ of the resonant cavity, preferably 1,064 nm, and mirror 11 is highly transmittive at the pumping wavelength, preferably 808 nm. Using a Nd:YAG crystal as the solid state laser medium and a resonating beam of about one millimeter in diameter, circulating power greater than 400 Watts can be attained within the resonant optical cavity curing operation.

An actuator 17, preferably a semiconductor diode laser, provides a light output, preferably at 808 nm, that is optically coupled to solid state laser 7 within resonant optical cavity 5. As indicated in the FIGURE, the light output 19 from actuator 17 is coupled and focused through lens 21 into input end 23 of fiber optics 25, preferably consisting of one or more optical fibers.

When resonant optical cavity 5 is within a specific environment, such as a process and/or harsh environment, fiber optics 25 extends into the specific environment and when the specific environment is contained within a chamber, or enclosure, 27, such as by housing 29, fiber optics 25 is enclosed in an optical feedthrough 31, preferably a vacuum feedthrough where a vacuum is established in the chamber, extending through the housing wall.

Light emerging from the output end 33 of fiber optics 25 is coupled and focused by lens 35 through mirror 11 into solid state laser medium 7 within resonant optical cavity 5 to end-pump the solid state laser medium. Positioning of the output end of fiber optics to end-pump a Nd:YAG crystal is shown, for example, in U.S. Pat. No. 4,723,257 to Baer et al.

Sensing region 9 could, in some applications, be within the specific environment, but not within a resonant cavity, and have light directed thereto from a light source within or outside the specific environment and/or actuated by a light provider outside the specific environment with light, when provided outside the specific environment, being optically coupled into the specific environment.

Sensing region 9 is capable of having particles thereat, such as, for example, contaminating particles when in a process environment with the sensing region preferably being positioned adjacent to the item, such as a wafer, being processed. Particles at the sensing region affect light, such as for example, where light is scattered (elastic or inelastic), produced and/or emitted by the particles, at the sensing region during operation of the device, and affected light 37 is collected by optical system, or light collector, 39 (a lens system as shown in the FIGURE) and coupled and focused through lens system 39 into input end 41 of fiber optics 43, preferably a fiber bundle for rectangular-to-circular light collection to light coupling.

A 20 mm$^2$ sensing region is preferably optically defined, or established, within resonant optical cavity 5 by use of an optical system having a magnification of 0.5, a 10 mm fiber bundle, and a 1 mm diameter beam, and affected, or scattered, light, preferably deviated at a 90° angle by particles at the sensing region, is collected for optical coupling from resonant optical cavity 5.

The affected, or scattered, light photons are coupled from the specific environment through fiber optics 43 and when the specific environment is contained within a chamber by housing 29, the fiber optics are enclosed in an optical feedthrough 45, preferably a vacuum feedthrough where a vacuum is established within the chamber, extending through the housing wall.

The light emerging from the output end 47 of fiber optics 43 outside the specific environment is collimated by lens 49, and the collimated light is then coupled through filter 51, preferably a 1.064 nm notch filter, and then coupled through lens 53 to light detector 55 of processor 57, and, more particularly, is preferably focused onto one or more photodetectors serving as light detector 55.

Light received at light detector 55 is converted into an electrical output at the light detector, amplified if needed, and then coupled to an analyzer for further processing, such as pulse height analyzing circuitry 59, preferably connected with microprocessor 61 for information interpretation, display and/or storage. Light collection and processing of collected scattered light may be achieved, for example, as shown in U.S. Pat. Nos. 4,571,079 and 4,798,465 to Knollenberg.

As can be appreciated from the foregoing, only optical elements, or components, are utilized within the specific environment, such as a processing chamber, and elements that might be adversely affected by a process or harsh environment are maintained outside the specific environment with optical coupling being utilized between the elements inside and outside the specific environment. An improved detection device with superior performance is achieved due to smaller size, greater sensitivity, higher reliability, and/or greater flexibility in location of the sampling region.

What is claimed is:

1. A device for in-situ detection of particles in a specific environment, said device comprising:
   a light provider positioned outside the specific environment;
   an optical coupler for coupling light from the light provider into the specific environment;
   a light source within the specific environment and responsive to said light provider for providing light received from the optical coupler;
   a sensing region within the specific environment, said sensing region being capable of having particles therein and receiving light from said light source whereby light is affected by particles at said sensing region;
   a resonant optical cavity wherein said light source is a laser medium within said resonant optical cavity, said resonant optical cavity also having said sensing region therein;
   a light collector within the specific environment for collecting light affected by particles at said sensing region;
   a second optical coupler for coupling affected light collected by said light collector from the specific environment; and
   a processor positioned outside the specific environment for receiving said affected light from said second optical coupler and, responsive thereto, providing an output indicative of particles detected at said sensing region causing said light to be affected.

2. The device of claim 1 wherein said laser medium is a solid state laser medium within said resonant optical cavity.

3. The device of claim 2 wherein said solid state laser medium is a Nd:YAG crystal.

4. The device of claim 2 wherein said light provider includes an actuator, said actuator providing a light output suitable for actuating said solid state laser medium.

5. The device of claim 4 wherein said actuator is a semiconductor diode laser.

6. A device for detection of particles in a harsh environment, said device comprising:
   a resonant optical cavity having a laser medium therein, said resonant optical cavity being positioned within the harsh environment and having laser light therein when in operation;
   an actuator positioned outside said harsh environment:
   an optical coupler for coupling light from said actuator into said harsh environment for actuating said resonant optical cavity;
   a sensing region within said resonant optical cavity, said sensing region being capable of having particles thereat and said sensing region receiving light in said resonant optical cavity whereby said particles scatter light at said sensing region;
   an optical light collector within the harsh environment for collecting light scattered by particles at said sensing region;
   a second optical coupler for coupling scattered light collected by said optical light collector from the harsh environment; and
   a processor positioned outside the harsh environment for receiving said scattered light from said second optical coupler and, responsive thereto, providing an indication of particles detected at said sensing region causing said light to be scattered.

7. The device of claim 6 wherein said laser medium in said resonant optical cavity is a solid state laser medium, and wherein said actuator includes a semiconductor diode laser providing said light output through said optical coupler into said resonant optical cavity to pump said solid state laser medium.

8. The device of claim 6 wherein said optical coupler and said second optical coupler include fiber optics and lenses for focusing light into and out of said fiber optics, and wherein said second optical coupler also includes a notch filter through which said scattered light passes to said processor.

9. The device of claim 6 wherein said harsh environment is contained in a housing, and wherein said optical coupler and said second optical coupler include an optical feedthrough for coupling of light through said housing.

10. The device of claim 6 wherein said laser medium and said optical light collector positioned within the harsh environment are optical elements, and wherein said processor positioned outside the harsh environment includes electrically active elements.

11. A device for in-situ detection of particles in a harsh process environment, said device comprising:

a resonant optical cavity within the harsh process environment, said resonant optical cavity having a solid state laser medium therein with said solid state laser medium being capable of providing laser light in said resonant optical cavity;

a semiconductor diode laser positioned outside said harsh process environment and providing a light output;

a first optical coupler for coupling said light output from said semiconductor diode laser to said solid state laser medium for end-pumping of said solid state laser medium whereby said solid state laser medium is caused to provide said laser light in said resonant optical cavity;

a sensing region within said resonant optical cavity, said sensing region being capable of having particles thereat, and said sensing region receiving said laser light within said resonant optical cavity whereby particles at said sensing region scatter light in said sensing region;

an optical light collector for collecting light scattered by particles at said sensing region;

a second optical coupler for coupling scattered light collected by said optical light collector from said harsh process environment, said second optical coupler collimating said scattered light;

a light detector for receiving said collimated scattered light from said second optical coupler and providing an electrical signal output derived from said received scattered light; and an analyzer for receiving said electrical signal output from said light detector and, responsive thereto, providing an output indicative of particles causing said light to be scattered at said sensing region.

12. The device of claim 11 wherein said light detector includes at least one photodetector.

13. The device of claim 11 wherein the harsh process environment includes a vacuum established therein with the harsh environment being contained within a housing, wherein said first and second optical couplers include a vacuum feedthrough for coupling light through said housing, and wherein said first and second optical couplers also include fiber optics and lenses for focusing said light into and out of said fiber optics.

14. A method for in-situ detection of particles in a harsh environment, said method comprising:

providing a light source within the harsh environment wherein said light source includes a resonant optical cavity responsive to a laser for to provide light therein;

providing a sensing region in the harsh environment with the sensing region having particles thereat and receiving light from said light source whereby light is scattered at said sensing region by particles at said sensing region and wherein said sensing region is within said resonant optical cavity;

collecting light scattered at said sensing region by said particles;

optically coupling the collected scattered light from the harsh environment; and using the collected scattered light coupled from the harsh environment to provide an indication of particles detected at the sensing region causing the light to be scattered.

15. The method of claim 14 wherein said method includes providing a solid state laser medium within said resonant optical cavity, and providing a semiconductor diode laser outside the harsh environment with said semiconductor diode laser providing said light output that is optically coupled into said resonant optical cavity to pump said solid state laser medium.

16. The method of claim 15 wherein the harsh environment is in a process tool, and wherein said method includes positioning said resonant optical cavity near the item being processed by said process tool.

17. The method of claim 15 wherein said method includes using fiber optics and lenses to optically couple said light from said semiconductor diode laser to said resonant optical cavity in the harsh environment, and using fiber optics, lenses and a notch filter to optically couple and collimate said collected scattered light from the harsh environment for use in processing said indication of detected particles.

18. The method of claim 17 wherein said method includes containing the harsh environment within a housing and utilizing an optical feedthrough for optically coupling light to and from the harsh environment.

* * * * *